United States Patent
Aksit et al.

(10) Patent No.: US 9,002,433 B2
(45) Date of Patent: Apr. 7, 2015

(54) SYSTEM AND METHOD FOR IMAGE-BASED INTERVENTIONAL DEVICE TRACKING AND SCAN PLANE GUIDANCE

(75) Inventors: Pelin Aksit, Columbia, MD (US); Shashank Sathyanarayana, Baltimore, MD (US); Meiyappan Solaiyappan, Ellicott City, MD (US); Ergin Atalar, Ankara (TR)

(73) Assignees: General Electric Company, Schenectady, NY (US); John Hopkins University School of Medicine, Baltimore, MD (US)

( * ) Notice: Subject to any disclaimer, the term of this patent is extended or adjusted under 35 U.S.C. 154(b) by 2672 days.

(21) Appl. No.: 11/532,446

(22) Filed: Sep. 15, 2006

(65) Prior Publication Data

US 2007/0249934 A1 Oct. 25, 2007

Related U.S. Application Data

(60) Provisional application No. 60/793,394, filed on Apr. 20, 2006.

(51) Int. Cl.
| | |
|---|---|
| *A61B 5/055* | (2006.01) |
| *A61B 19/00* | (2006.01) |
| *G01R 33/34* | (2006.01) |
| *G01R 33/483* | (2006.01) |
| *G01R 33/28* | (2006.01) |
| *G01R 33/54* | (2006.01) |
| *G01R 33/56* | (2006.01) |

(52) U.S. Cl.
CPC .............. *A61B 5/055* (2013.01); *A61B 19/5244* (2013.01); *G01R 33/34084* (2013.01); *G01R 33/4833* (2013.01); *A61B 2019/5236* (2013.01); *A61B 2019/5251* (2013.01); *A61B 2019/5295* (2013.01); *G01R 33/287* (2013.01); *G01R 33/543* (2013.01); *G01R 33/546* (2013.01); *G01R 33/5608* (2013.01)

(58) Field of Classification Search
USPC ................. 600/407, 409–411, 414, 424, 426; 324/307, 309
See application file for complete search history.

(56) References Cited

U.S. PATENT DOCUMENTS

| | | | | |
|---|---|---|---|---|
| 6,554,771 | B1 * | 4/2003 | Buil et al. ...................... | 600/459 |
| 6,708,054 | B2 * | 3/2004 | Shukla et al. ................. | 600/411 |
| 2004/0044279 | A1 * | 3/2004 | Lewin et al. .................. | 600/407 |
| 2004/0171924 | A1 * | 9/2004 | Mire et al. .................... | 600/407 |

OTHER PUBLICATIONS

Solaiyappan, M., et al., "Depth Reconstruction from Projection Images for 3D Visualization of Intravascular Probes," ISMRM Proc. 1999.

* cited by examiner

*Primary Examiner* — Mark Remaly
(74) *Attorney, Agent, or Firm* — Ziolkowski Patent Solutions Group, SC

(57) ABSTRACT

An MR system and method for tracking a device of an interventional procedure within a scan subject is disclosed. At least two MR projections of the device are acquired, from which 3D coordinates of the device are determined. Subsequent image acquisition is adjusted with respect to the coordinates of the device to guide movement thereof towards target anatomy. The present system and method provide the ability to locate and visualize continuous portions of an interventional device in 3D, and do not require the use of embedded RF localizing coils.

20 Claims, 8 Drawing Sheets

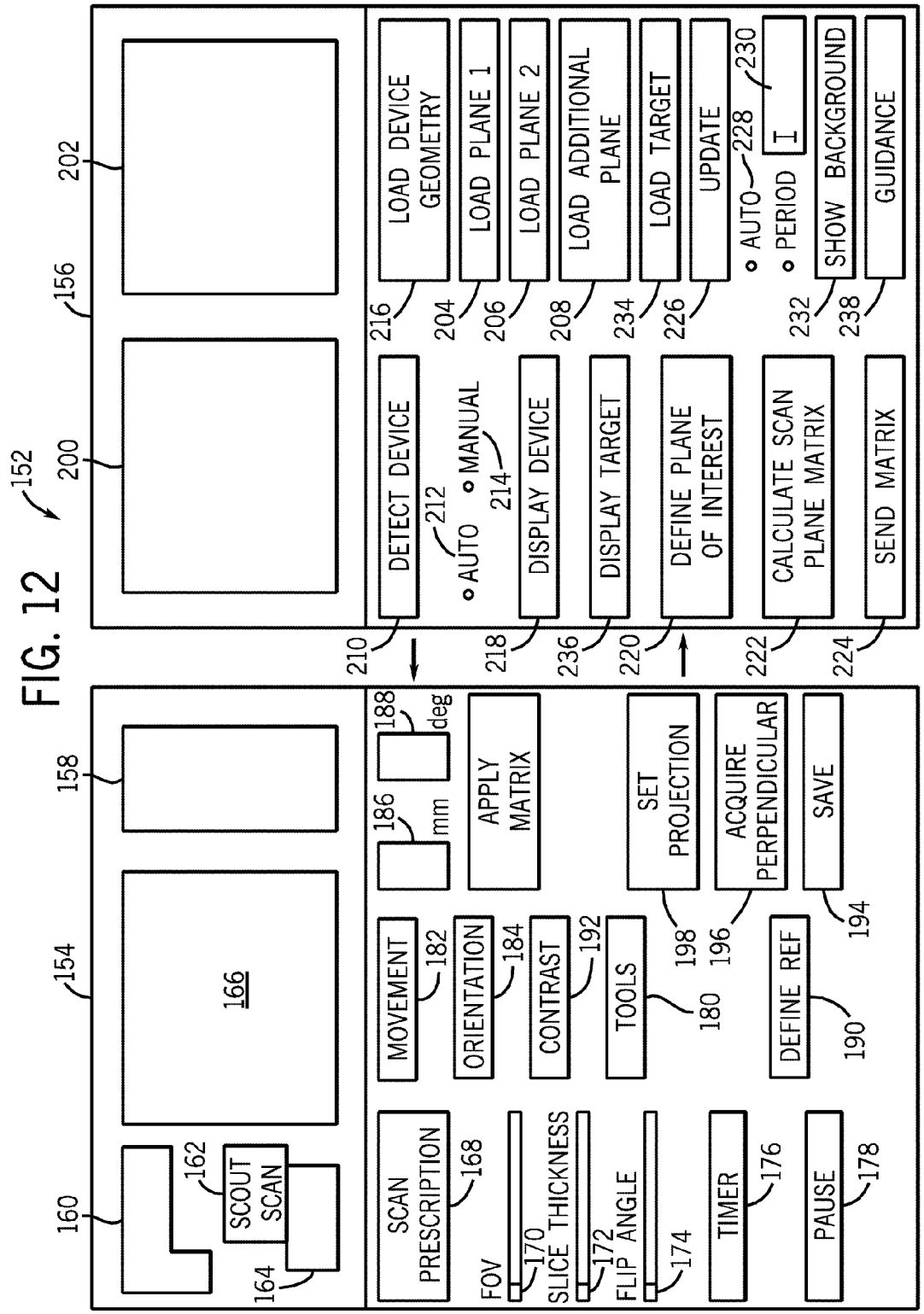

United States Patent 9,002,433 B2

SYSTEM AND METHOD FOR IMAGE-BASED INTERVENTIONAL DEVICE TRACKING AND SCAN PLANE GUIDANCE

CROSS-REFERENCE TO RELATED APPLICATION

The present invention claims the benefit of U.S. provisional application Ser. No. 60/793,394, filed Apr. 20, 2006, incorporated herein by reference.

BACKGROUND OF THE INVENTION

The present invention relates generally to MR imaging and, more particularly, to a system and method for tracking and visualizing interventional devices, such as catheters, via MR imaging to orient and guide real-time procedures without the need for localizing or embedded RF coils.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_Z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques. Such techniques have increased the rapidity of image reconstruction to the point where real-time or near real-time imaging can take place.

Interventional and invasive medical procedures, in which implements are manipulated within a scan subject, are instances in which real-time MR imaging is particularly useful. It is often helpful to provide tracking and visualization of the position and orientation of interventional implements and devices to quickly and efficiently conduct these procedures.

Initial methods for visualizing and guiding interventional devices during medical procedures relied on a medical professional's ability to guess the orientation and location of an interventional device from a number of 2D images and background knowledge of subject anatomy, for both active and passive devices. In these methods, MR images of the implement are taken from a number of angles and displayed to the user. From these images, a user had to mentally interpolate the 3D orientation and location of the device with respect to the surrounding and target anatomy. Such methods are inconvenient for doctors and have slow response times to device movement because multiple images at various angles must all be continually refreshed.

Currently the most commonly used active method for interventional device visualization and guidance involves the use of embedded RF coils. The implements used in an interventional procedure are specifically created to contain a number of tiny RF coils (on the order of a few millimeters) embedded therein to provide a way to localize the position of the implements. MR signals acquired along multiple axes are used to localize the RF coils embedded in a device. At best, this method may be modified to visualize an approximated extended length of the device by embedding a large number of RF coils along its length. Nonetheless, MR images of devices incorporating RF coils appear as a series of bright dots from which the body of the device is generally extrapolated or assumed. The drawbacks of this method are that embedding micro-coils in medical implements constrains their geometry and mechanical properties when precision is important. While increasing the number of coils used improves the signal received, reducing the number of coils to allow flexibility in device geometry may result in insufficient localizing information. Thus, a tradeoff exists between geometric/mechanical device precision and imaging/localizing precision. Such imprecision in either form is undesirable for procedures that require tracking of multiple points and precise prediction and display of device response to user interaction.

However, in addition to device localization, visualizing extended lengths of devices is useful in interventional procedures. Visualization methods that make extended lengths of interventional devices appear bright with respect to the background have been performed using both passive and active techniques. Passive visualization techniques, such as filling a catheter with contrast agents like gadolinium, have inherently lower signal to noise ratios as compared to active imaging techniques. Such techniques also impose mechanical limitations on devices—if the lumen is filled with a contrast agent, it can't be used for additional device or substance delivery which may be essential to the procedure.

Extended lengths of interventional devices can be made to appear brighter with respect to the background by using other active techniques. For example, some methods utilize active RF antennas for improved visualization in MR images in the form of an elongated loop style or loopless style, and provide increased visual contrast in reconstructed MR images of extended length of devices. Various interventional devices such as catheters may be formed from, or may include, active RF antennas where extended lengths of devices are better visualized.

Active antennas that make extended lengths of devices appear bright are preferable since they are more conspicuous in MR images as they move within the body (as compared to passive techniques), yet do not increase device size (as do embedded RF coils, which are also active antennas). However, while these active antennas, which do not utilize embedded RF coils, can be used for imaging and imaging-based tracking methods, signals from these antennas are not generally usable to determine the location of a device within a body. For example, a user could not generally rely upon a localizing signal from the antenna to guide the MR acquisition scan plane thereto. Some methods exist wherein a combination of continuous active antennas and RF localizing coils are employed, but no method is presently known in which an entire or continuous length of an interventional device can be imaged and localized, without the use of embedded RF localizing coils. This same problem of localization also exists for passive devices, such as gadolinium filled catheters, where an extended portion of the device can be visualized but not localized.

Inherent to most current visualizing and tracking methods is the inconvenience of lost depth information. That is, depth information is generally lost in MR images of interventional devices (acquired by any of the above-mentioned techniques), causing a sometimes misleading device appearance. When an image of a device is overlaid on a "roadmap" or anatomical reference image, the entire device appears in front of all the anatomy in the roadmap image. Some adaptations have been developed to deal with these issues, but still present drawbacks. Computing 3D shapes from 2D projections, using fast bi-planar approaches and slower projection reconstruction approaches can be used to eliminate the depth anomaly that occurs when projection images are displayed on roadmaps. In such methods, device projection images are artificially blended semi-transparently into the reference image after acquisition so that the parts of the device existing below the reference image slice appear dim, while the portions above the reference image slice appear bright. However, such methods are not intended for, and do not provide, guidance of an interventional device for manipulation during a procedure. That is, the MR acquisition scan plane is not adjusted to track the interventional device or aid in interventional device placement.

It would therefore be desirable to have a system and method capable of directly and precisely obtaining the orientation and location of interventional devices with respect to the surrounding anatomy without the use of localizing RF coils. It would be further desirable for such a system and method to provide visualized guidance in real-time of device plane images with actual target anatomy so that operators will not be required to depend so heavily on experience with scan subject anatomy, device geometry, and device characteristics.

BRIEF DESCRIPTION OF THE INVENTION

The present invention provides a system and method of tracking and visualizing interventional devices in scan subjects in real time without requiring the use of embedded RF coils that overcomes the aforementioned drawbacks. The invention generally includes acquisition of 2D projections, device detection on the 2D projections, and 3D device shape determination from the 2D projections. The invention also may provide for selection of a scan plane of interest and/or guidance of the scan plane towards a target plane. Thus, interventional devices may be tracked that could not previously be tracked and the extended lengths of these devices can then be visualized.

In accordance with one aspect of the invention, an MRI system includes a plurality of gradient coils positioned about a bore of a magnet to impress a polarizing magnetic field, an RF transceiver system and an RF switch controlled by a pulse module to transmit and receive RF signals to and from an RF coil assembly. The system also includes a computer programmed to acquire a number of 2D MR projections from the transceiver system, and then locate and determine an orientation of a continuous portion of an interventional device in 3D using the 2D MR projections.

In accordance with another aspect of the invention, a method for tracking an interventional device is disclosed. The method includes acquiring two or more MR images that do not lie in the same plane, locating an interventional device within the images, and reconstructing a 3D shape of the interventional device from the images. The technique also includes determining a plane of interest with respect to the device and adjusting MR image acquisition to generally coincide with the plane of interest.

In accordance with a further aspect of the invention, the invention is embodied in an MR guidance interface stored on a computer readable storage medium. The interface includes an MR projection acquisition control, a device detection tool, a 3D reconstructor, a user input, and a guidance window. The device detection tool indicates the location of an interventional device in MR projections and the 3D reconstructor determines the 3D coordinates thereof. The user input allows a user to then define a scan plane with respect to the 3D coordinates. A display of the scan plane and a target plane is presented in a guidance window.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 12 is an exemplary guidance interface in accordance with the present invention.

DETAILED DESCRIPTION OF THE PREFERRED EMBODIMENT

A system and method of the present invention are hereinafter described that is capable of locating, and determining a shape and an orientation of implements used in interventional or invasive procedures. Though the present invention finds particular utility in tracking particular types of interventional devices for medical procedures, it is recognized that the present invention also encompasses a broad class of contrast mechanisms, recognition methods, devices, and procedures. This also includes non-medical procedures, and those involving the use of implements with negative MR contrast.

Figure 1:
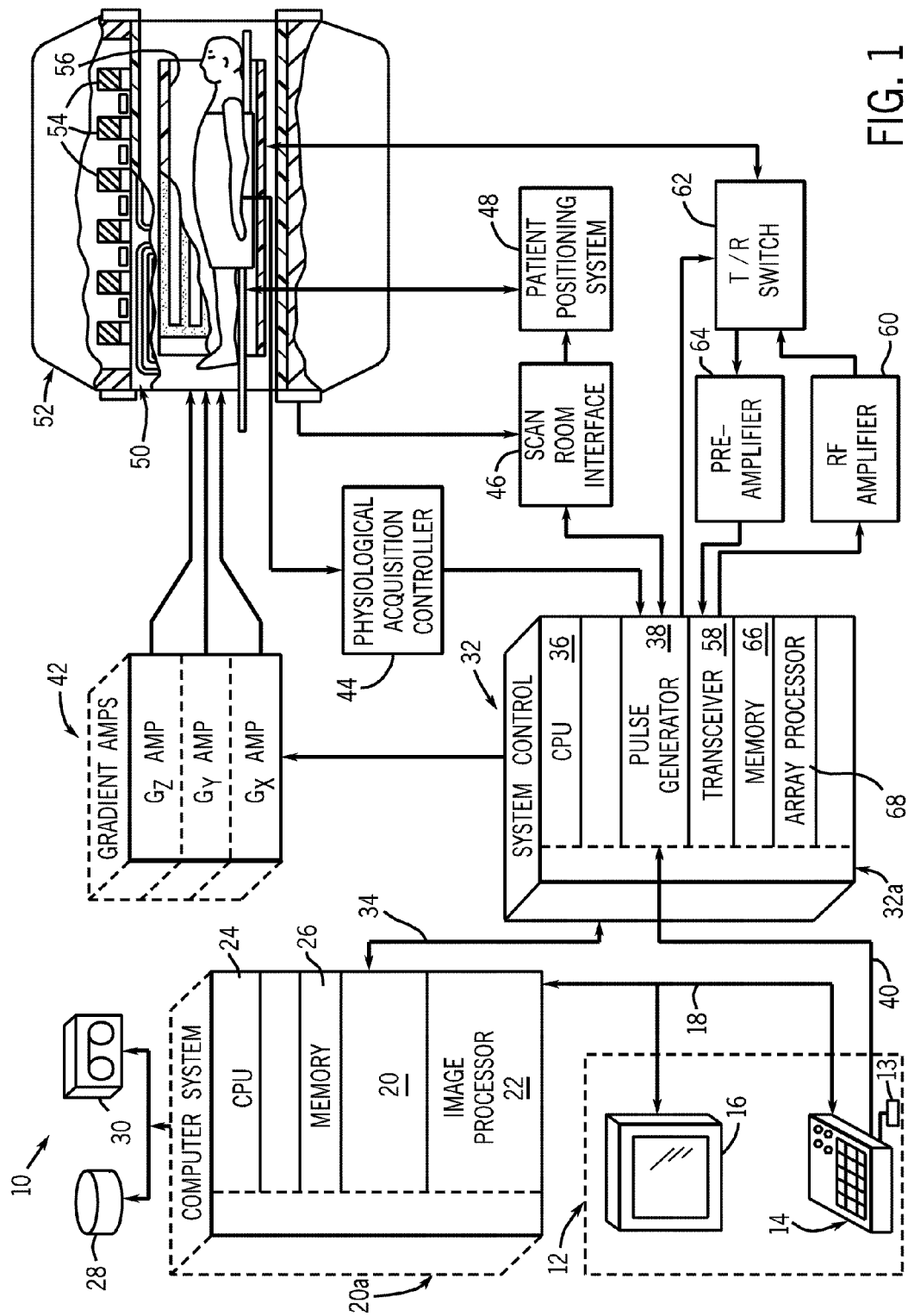
FIG. 1 is a schematic block diagram of an MR imaging system for use with, and incorporating, the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

In a preferred embodiment, MR system 10 has the ability to accept requests for and provide projection images in real-time and the ability to accept external direct control of the scan plane. Thus, the scan console 12, computer system 20, and/or system control 32 may be used to automatically monitor projection image updates from the scanner in real-time, determine interventional device location on the projection images, find the device orientation in the region of interest, and other guidance related tasks discussed below.

Figure 2:
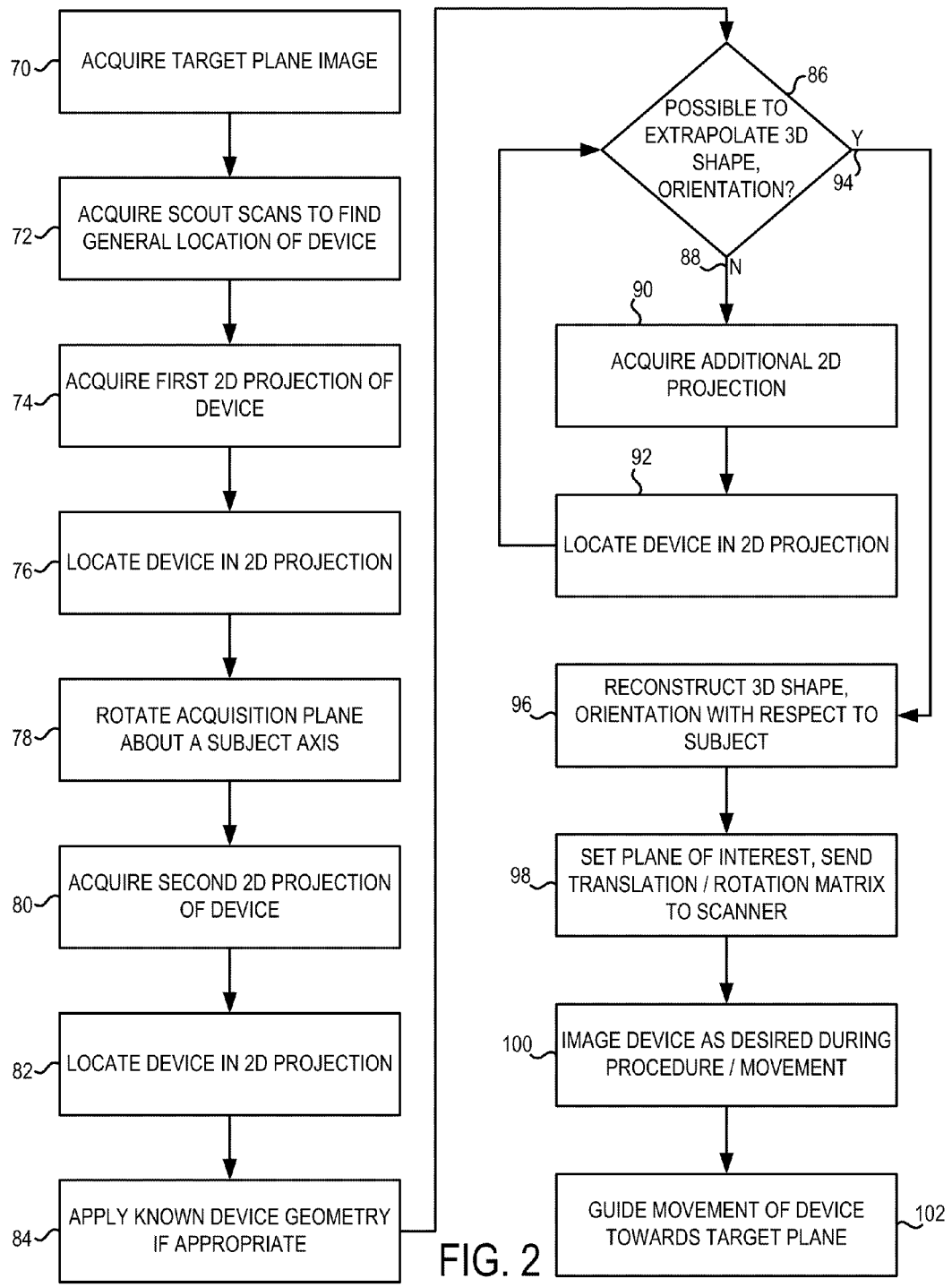
FIG. 2 is a flow chart in accordance with one aspect of the present invention.

Referring now to FIG. 2, a flow chart generally setting forth a technique of the present invention is shown, from which an overview of the technique will be discussed. Subsequent figures will discuss portions of the technique in detail. The technique of FIG. 2 begins with MR acquisition of a target plane image 70. A target plane includes a scan subject's anatomy of interest in a plane favorable or significant to an invasive or interventional procedure. For example, a target plane image might contain a particular artery of significance in an interventional medical procedure. The target plane may be located via scout scans, or based upon a priori knowledge of the scan subject. To determine the general locality within the scan subject of an interventional device of the procedure, scout scans are taken to find the device 72, though background knowledge of the subject's anatomy and location of the device therein may also be used in some instances. Thus, embodiments of the present invention may be "scoutless," relying upon known localization techniques or those described below to locate a device within the bore of an MR scanner. Once the device is generally found, a 2D MR projection of the device is acquired at a first angle 74. The technique identifies the device within the 2D MR projection 76, which may be done either manually or automatically. The MR acquisition plane is then rotated a specified angle from the plane of acquisition of the first 2D projection 78. This rotation preferably takes place about the longitudinal axis of the patient, but may take place about other axes as desired. Another 2D MR projection is then acquired of the device at this second angle 80, and the device is similarly located therein 82. In a preferred embodiment, these 2D MR projections are orthogonal.

In some instances, the 3D shape and/or volume of the interventional device is known to a certain degree of precision prior to the start of the interventional procedure. If a device is mostly linear or planar, and has no loops or other non-uniformities, the known device geometry may be applied 84 to the 2D projection data to simplify the forthcoming 3D reconstruction. In any event, the technique examines whether sufficient data (in the form of 2D coordinates and/or known geometry) exists to reconstruct a 3D shape and orientation of the interventional device 86. If more data is needed 88, the present invention acquires an additional 2D projection at another angle 90 and locates the device therein 92. After the additional projection is acquired, the invention reevaluates whether it is possible to extrapolate the 3D shape and orientation of the device 86. When enough coordinate data is obtained, the invention reconstructs the 3D shape and orientation of the interventional device 96 with respect to the scan subject and/or target plane.

Once the 3D shape and orientation are obtained, the present invention provides for a determination of a scan plane or plane of interest of the device 98. That is, various planes including, or in close proximity to, an interventional device may be imaged for purposes of tracking. Once a plane of interest is set, a matrix is determined and sent to the MR scanner indicating a degree of rotation or a distance of translation necessary to align the current plane of acquisition with the desired plane of interest. During the course of the invasive/interventional procedure, the plane of interest may be continuously or periodically re-imaged to reflect movement of the device 100. Ultimately, the present invention guides movement of the device in terms of position and orientation such that a user can align the device or the plane of interest 102 with the target plane or another plane defined with respect to the subject anatomy that prescribes a desired orientation of the device considered favorable to the interventional procedure.

Figure 3:
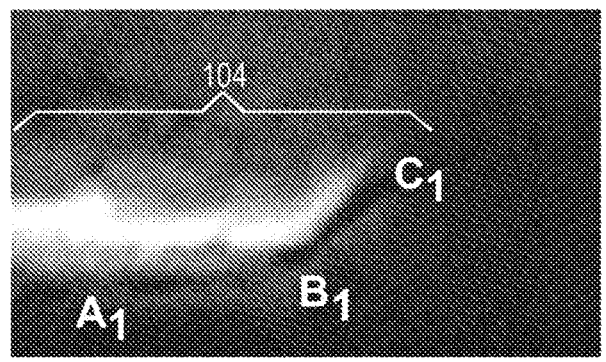
FIG. 3 is an exemplary MR image in accordance with the present invention.
Figure 4:
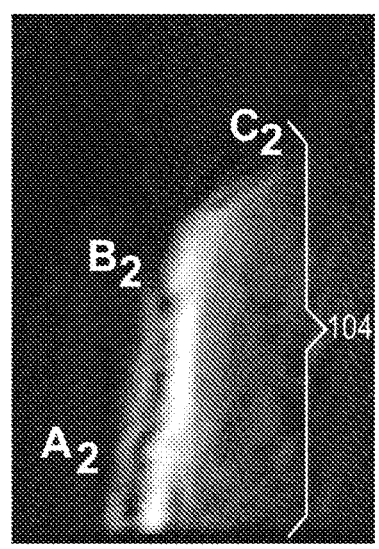
FIG. 4 is an exemplary MR image in accordance with the present invention.

Referring now to FIGS. 3 and 4, a pair of 2D projection images containing an interventional device 104 is shown. As discussed above, 2D projection images are used in the present invention for reconstructing an interventional device's location, shape, and/or orientation within the scan subject. In some embodiments of the present invention, scout scans have already been taken prior to the 2D projection image acquisition to locate the target plane or determine where the device is generally located. The images depicted in FIGS. 3 and 4 represent images that may be acquired in real-time via a SSFP sequence, though the projections may be acquired by other known 2D methods such as fast GRE acquisition.

The scan plane of acquisition for these 2D projection images may be set and adjusted by a user before commencement of the procedure or in real-time during the procedure. Alternatively, the scanner may be configured to acquire orthogonal projections in the sagittal and coronal planes by default. Further 2D projections may be requested or automatically acquired as needed. Preferably, the 2D projections are acquired such that slices are not taken through the primary length of the device, but rather are acquired across or along the length of the device to avoid unnecessary complexity in reconstruction due to projection overlaps.

After the first 2D projection is acquired and before the second 2D projection is acquired, the scan plane of the MR scanner is rotated by a specified angle. For primarily linear or planar devices, this angle may be 90 degrees. Identification of the interventional device within the 2D projection images may take place between acquisitions or after both are acquired. To aid in this respect, extended lengths of the interventional device, and any secondary structures within its volume, are imaged to appear without background anatomy. Known tissue and fat suppression techniques may be employed to improve the visualization of the device and significant surrounding anatomy. In a preferred embodiment, a scanner used in accordance with the present invention is equipped with real-time control of lipid suppression and inversion recovery.

As seen in FIGS. 3 and 4, the interventional device 104 appears as a bright line closely neighbored by a dark shadow. As one of skill in the art will recognize, this imaging phenomenon is caused by the field cancellations of an active antenna. These signal cancellations occur due to the interaction of the circular reception field of the antenna with the homogeneous field of the transmit body coil, causing the antenna to have a dark line with a bright band adjacent to it in an image projection. Thus, an interventional device 104 used in accordance with the present invention may preferably be a receive-only active antenna or may contain such an antenna. Alternatively, antennas may be used that are operable in both transmit/ receive modes, as well as other devices exhibiting appropriate contrast in MR images. Notably, an interventional device 104 used in association with the present invention need not contain embedded RF localizing coils, which would appear as individual bright dots in a 2D projection image. By avoiding the need for RF localizing coils, the whole volume of a device 104 is visible in the bright/shadow contrast of an image projection.

Though the device 104 appears visible to the human eye in a reconstructed image, the extent of the device must be somehow identified to the scan system. The present invention provides for both manual and automatic detection of interventional devices within 2D projection images. In embodiments where automatic detection is to be used, the interventional device should be such as to exhibit a detectable change in contrast when appearing in a 2D projection. For example, active antenna type devices 104 as shown in FIGS. 3 and 4 are used to provide increased, detectable contrast in images. The rapid change in contrast exhibited by such devices is used to detect them automatically. In a preferred embodiment, each row and or column of the projection image may be examined by the system, and the difference between the maximum and minimum intensity values therein will be stored as the contrast of the row. The areas having maximum contrast change are identified as the interventional device.

If manual detection is to be used, a user interface (discussed below) permits a user to touch or click on a number of points along the length of the device 104 in each projection to define a location of the device. The points should correspond in the two images, though the degree of correspondence will be proportionate to the number of points. From the user's identification, the scan system may then interpolate a continuous length from the points. It is appreciated that embodiments of the present invention may use or provide for both automatic and manual locating of interventional devices in 2D projections.

In FIG. 3, three points along the continuous length of the device 104, A1, B1, C1, are noted. Correspondingly, the same three points of the device 104 are noted in FIG. 4 as A2, B2, C2. These points reflect a length of the device A1, A2, a bend in the device B1, B2, and a tip of the device C1, C2. It is to be appreciated, however, that the points along the length of the device to be noted will vary according to the device geometry. Any two identified points are sufficient for a rectilinear device, assuming that such device is rotationally uniform. Only three corresponding points A1-C1, A2-C2 of interventional device image 104 on the 2D projection images of FIGS. 3 and 4 need be identified to determine the spatial orientation of the device 104. That is, for non-uniform rectilinear devices and for planar devices such as shown, three identified non-collinear points per projection are sufficient. However if the device shape assumes arbitrary bending, it will be necessary to obtain the entire device shape profile data for a more comprehensive determination of the three dimensional shape in the ensuing steps. For orthogonal projections, these sets of points will exist in X-Z and X-Y planes of the subject respectively.

Figure 5:
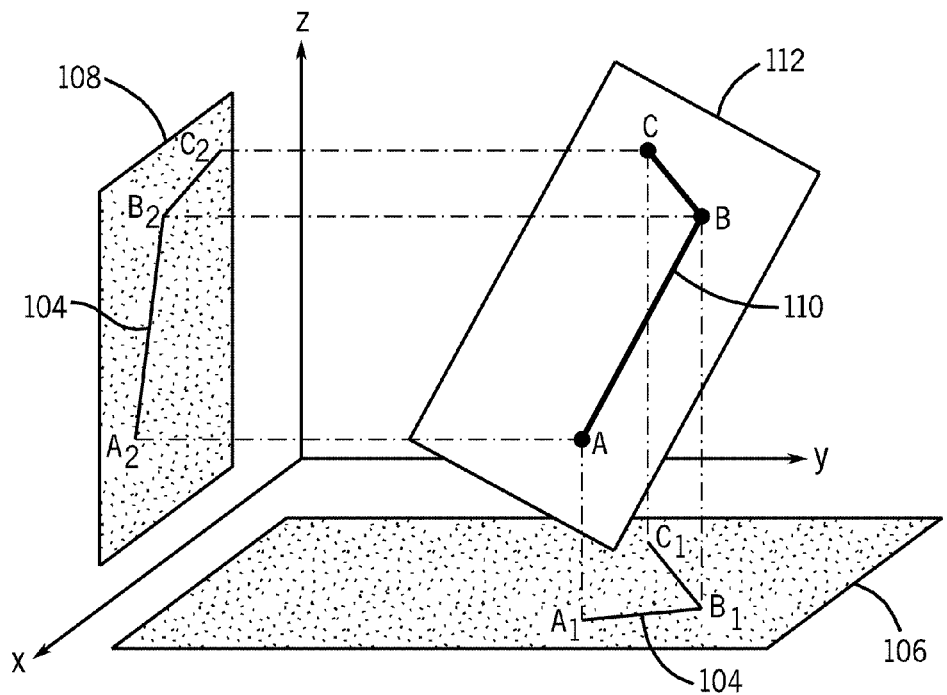
FIG. 5 is a 3D graphical representation in accordance with the present invention.

Referring now to FIG. 5, a visualization of 3D reconstruction from two orthogonal 2D projections is shown. Projection 106 corresponds to that shown in FIG. 3 and projection 108 corresponds to that shown in FIG. 4. The image of interventional device 104 appears in both projections 106, 108. Since each point in 3D space has a unique projection on distinct 2D projections, the image position of corresponding portions of an interventional device in 2D projections provides a basis for 3D reconstruction. In other words, the identified points or length of interventional device 104 in each projection 106, 108 are used to reconstruct a shape 110 and a positioning or orientation 112 of the interventional device 104 in 3D space.

In principle, any two biplanar non-coextensive projection images 106, 108 oriented in any two directions could produce the information required for resolving the spatial location, shape, and/or orientation of a linear continuous device such as a catheter. That is, if the device is known to be a linear single-bodied object, and if there aren't any loops or branches in the device, then a minimum of two projections is sufficient to rebuild the entire device in 3D. As shown, the interventional device shape 110 does not contain loops, so points in 3D space A, B, C have unique projections A1-C1, A2-C2 on distinct 2D projections 106, 108. Similarly, if branches, loops, or other sections of the device will not need to be imaged, as when for example, the known anatomy and procedure dictate that such non-uniformities will not be significant during a procedure, then only two projections will still be sufficient. It is to be understood that, while FIG. 5 shows the correspondence of only three sets of points along the length of interventional device shape 110, an actual reconstruction algorithm of the present invention may use exceedingly more points of correspondence to reconstruct essentially a continuous length or shape of a device.

Geometrically, the accuracy of the 3D reconstruction may be improved when the angle between the biplanes 106, 108 is closest to 90 degrees. Similarly, 3D reconstruction will be simplified when the projections contain a common axis. Thus, generally orthogonal biplanar projections 106, 108, as shown, are desirable. Computing 3D shapes from 2D projections is further simplified when a priori knowledge of the device shape and mechanical properties is used. In such a case, the shape 110 of a device is already known and only an orientation or positional plane 112 remains to be computed.

However, if the device contains non-uniformities such as loops or overlaps, two projection images may not suffice. Identified points along the length of the device in the two projections may not properly correspond if they represent overlapping segments or if they form part of a loop. The MR system of the present invention can accept user input or automatically determine whether a 3D reconstruction based upon a given number of projections is or will be accurate. If non-uniformities in correspondence due to overlaps or loops are detected, if the reconstructed image does not match prior knowledge of the device geometry, or if a user simply views the reconstruction and requests additional projections, the system can acquire such additional projections.

The additional projections may be automatically acquired or acquired upon request. Each additional projection is taken at an angle distinct from the initial two projections 106, 108, until sufficient views have been acquired to reconstruct the shape of the device including the extent of any loops, branches, or other non-uniformities thereof. The system may also be configured to initially acquire more than two projections if it is known that two will not suffice.

Once sufficient projections are acquired, a continuous length 110 of the interventional device is reconstructed. Prior systems relying on embedded RF coils provide reconstructions of merely a set of dots corresponding to the location of the coils, rather than a set of 3D coordinates of a continuous length of the device. Furthermore, a 3D reconstruction of the present invention provides an indication of the orientation 112 of the entire device in 3D with respect to one or both of the target plane and subject anatomy. Subsequent imaging of the device may take place in alignment with device orientation plane 112, or may be set to other planes.

Figure 6:
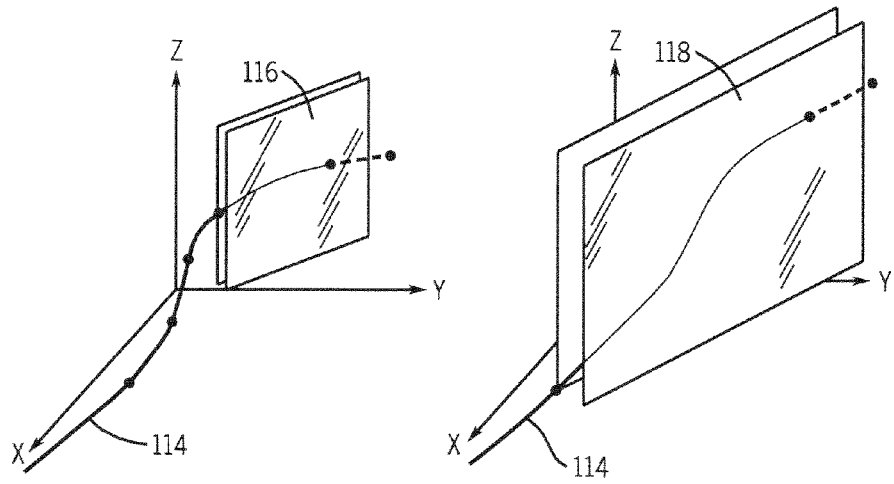
FIG. 6 is a graphical representation of exemplary MR scan plane orientations of the present invention.
Figure 6:
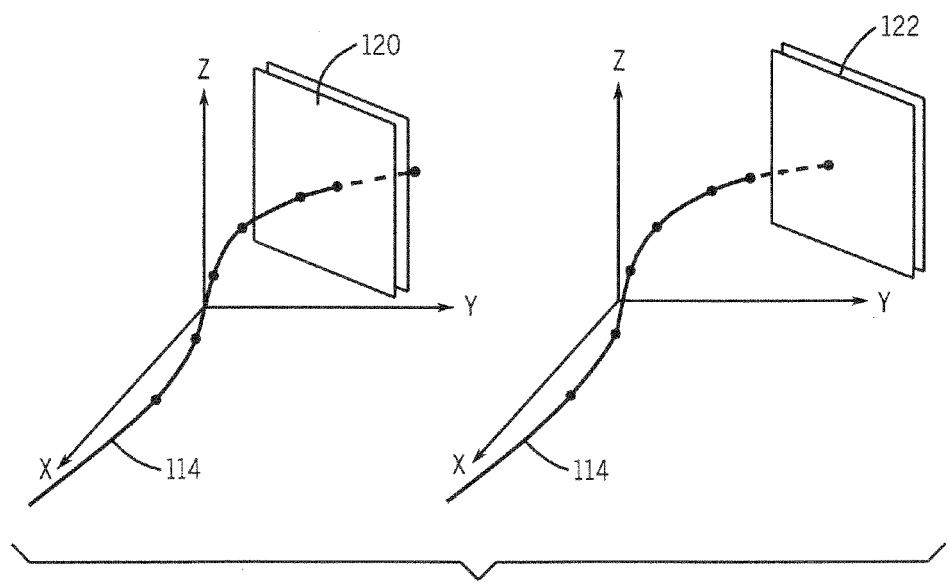

Referring now to FIG. 6, a number of orientations 116-122 of a desired scan plane or plane of interest are shown with respect to a 3D interventional device representation 114. Different interventional procedures require different portions of a device to be tracked and/or visualized. Further, the geometries of various invasive or interventional probes, scopes, catheters, needles, and the like, used in such procedures can vary substantially. Accordingly, a user may select a particular orientation of a current MR acquisition slice to track movement of the device, a portion of the device, or other significant procedure-related phenomena.

A user interface of the present invention therefore provides a user with adjustable scan plane orientations. FIG. 6 shows, for example, that a user may desire an orientation 116 in which the MR scanner will acquire a slice along the tip of interventional device 114. If a user selects an orientation 118, the MR scanner will image a slice along the majority of the length of interventional device 114. Alternatively, the desired scan plane may be selected to be perpendicular to device 114. In an electro-physiology (EP) ablation procedure, for example, it would be desirable to image ahead of the tip of the interventional device to monitor for excessive heat damage to tissue. Thus, FIG. 6 also shows a scan plane 120 perpendicular to and touching the tip of device 114 and a scan plane 122 perpendicular to and ahead of the tip of device 114. It is appreciated that many other orientations and positions of a desired scan plane or plane of interest exist, and will vary based upon the device used and the procedure being performed.

Alternatively, the desired scan plane or plane of interest 116-122 may be automatically determined. The type of interventional procedure may dictate the position of the scan plane, or statistical fitting methods may be used to determine the plane most aligned with device 114. Furthermore, the thickness of the scan plane 116-122 may also be adjusted by a user before or during the interventional procedure.

When the plane of interest is determined with respect to the 3D coordinates of the interventional device, a series of instructions, which may take the form of a translational and/or rotational matrix, is sent to the scanner from a processing unit or user interface to align current MR data acquisition with the plane of interest. Depending upon the location and orientation of the device, the matrix will relate a degree of rotation and/or a translation direction and distance such that MR acquisition coincides with the desired plane. As such, the MR scanner and user console of the present invention are equipped for real-time scan plane adjustment settings to be transmitted therebetween.

Figure 7:
FIG. 7 is an exemplary MR image in accordance with the present invention.

As shown in FIG. 7, the reconstructed image of the device in the desired scan plane, showing its 3D shape and orientation, is displayed to a user. In the image shown, the scan plane of interest was selected to occur along the longitudinal axis of the device, similar to that shown in FIG. 6 as example 118. During the interventional procedure, the image of the plane of interest may be continuously updated in real time, or may be refreshed periodically, or manually, to reflect motion of the device.

Figure 8:
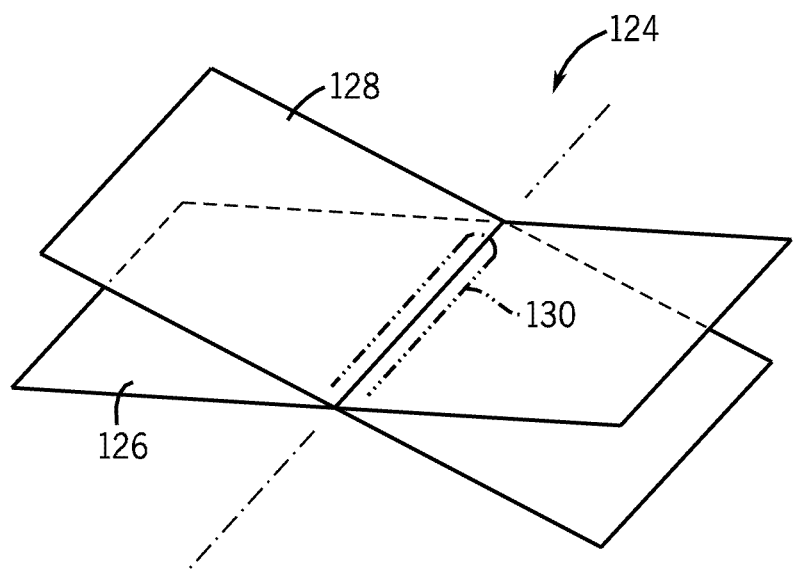
FIG. 8 is a graphical representation of an exemplary guidance visualization in accordance with the present invention.
Figure 9:
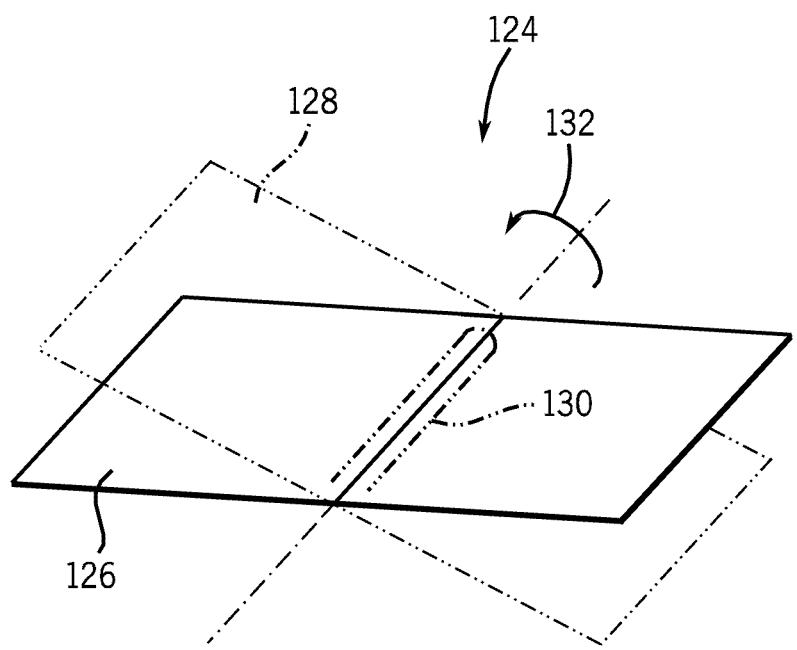
FIG. 9 is a graphical representation of another exemplary guidance visualization in accordance with the present invention.

Referring to FIGS. 8 and 9, an example visualization 124 from a guidance interface is shown. An image of the target plane 126 and the selected scan plane 128 are displayed together in a composite 3D image 124. The relative angle between the target plane 126 and scan plane 128 corresponds to the actual angle between the anatomy of the target plane and the orientation of the interventional device. Since the planes 126 and 128 intersect along the body of the device 130, a user will appreciate that only rotation of the device 130 is necessary to align the planes, not any amount of translation. If the planes intersected at some other axis, the composite image 124 would reflect the planes 126, 128 intersecting along a different line, or not intersecting at all. In such a case, a user would have a visual indication of the distance and direction between the target anatomy and the device.

FIG. 8 depicts an instance where a scan plane of interest 128 intersects a target plane 126 along the primary axis of an interventional device 130. Thus, the planes are shown having an angle therebetween. To align the significant portion of the interventional device in scan plane 128 with the anatomy of the target plane 126, such that their planes coincide (assuming such is favorable to the interventional procedure underway), a user will rotate the interventional device 130 by an amount 132 until they appear aligned in the visualization 124, as shown in FIG. 9. In other words, scan plane 128 rotates by angle 132 to target plane 126.

Figure 10:
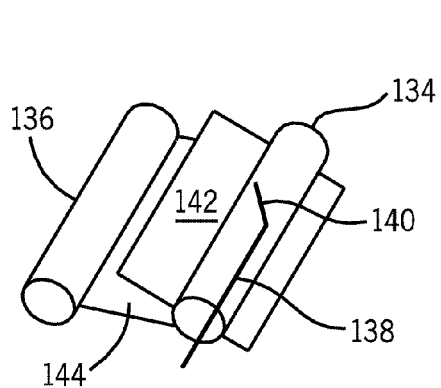
FIG. 10 a graphical representation of an interventional device in use in accordance with the present invention.

The present invention will now be described with respect to an exemplary interventional medical procedure for purposes of illustration. However, the invention is not limited to this or any other particular procedure. FIG. 10 shows a schematic illustration of a transcaval procedure for the creation of a mesocaval shunt. In this procedure, a transvascular puncture is made from the inferior vena cava (IVC) 134 to the superior mesenteric vein (SMV) 136 using an active needle/catheter 138 with an angled tip 140. Preferably, a loopless active antenna is used as the catheter 138 because it can have an elongated rigid shaft and a sharp tip for puncture procedures. A successful puncture can be made when the plane of the angled tip 140 lies within the target plane 144 that passes through both veins 134, 136.

As shown, a user has already acquired 2D projections to determine the 3D shape and orientation of needle 138, and has set a plane of interest, or catheter plane 142, to lie along the major axis 138 of the needle and to include the tip 140. It may also be desirable to view an extended part of the catheter 138 in addition to the tip 140, to provide maximum ability to maintain the orientation 142 of the device 138 during its subsequent advancement. Any twisting or warping of the body 138 of the device which could cause the tip 140 not to move in the expected direction can thus be compensated for. If the tip 140 were unexpectedly steered away from the desired course, consequent repositioning could cause injury to the vessels 134, 136 or other body parts.

By determining the catheter plane 142 and calculating the plane's orientation with respect to an initially prescribed target plane 144, the present invention provides information on the necessary rotation and translation of the interventional device 138 necessary for the tip 140 to reach the target plane 144 and SMV 136. Once the plane 142 of the angled tip 140 and adjoining sections of the catheter 138 is found, the present invention updates the current scan plane of the MR scanner accordingly, and provides exact directions for the rotation and manipulation required for arriving at the target plane 144. The puncture needle 138 should be well-positioned such that when it is manipulated for the puncture, the tip 140 should proceed precisely in the desired direction to enter into the SMV 136.

Figure 11:
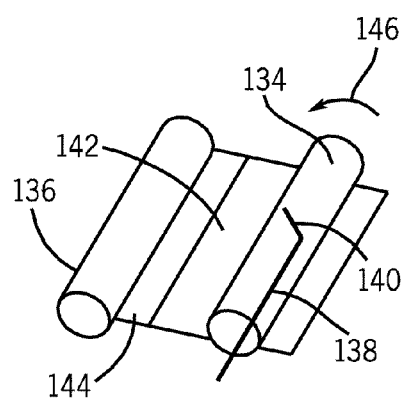
FIG. 11 is a graphical representation of another interventional device in use in accordance with the present invention.

FIG. 11 displays the result of a user counterclockwise rotation 146 of the catheter 138. The needle tip 140 now lies in the same plane 144 as veins, 134, 136. The catheter 138 can now simply be manipulated to extend its tip 140 through the IVC 134 and into the SMV 136. The user knew the proper amount of rotation needed to correctly align the tip 140 and its plane 142 with the target plane 144 from a guidance visualization. That is, an actual acquired target plane MR image will be shown intersecting the plane of the catheter tip image, in a manner similar to that shown in FIGS. 10 and 11. It is appreciated that alternatives to this visual method of guidance include arrows, other indicators, textual directions, audio directions, visual demonstrations, etc.

FIG. 12 shows a user interface 152 associated with the present invention. User interface 152 includes at least two different GUIs or display windows 154, 156. These windows 154, 156 may be displayed on a scanner console, a separate PC, other devices, or combinations thereof. Scan console window 154 represents a typical MR image acquisition screen. A reference window 158 displays images from optional reference scans to illustrate surrounding and overall scan subject anatomy to a user. Reference window 158 may depict where the current scan plane is located with respect to the remainder of the scan subject anatomy. A number of scout scans may be acquired and displayed in scout scan chart 160. Each scout scan is acquired when a scout scan control 162 is actuated and the resulting image is shown in scout scan viewing window 164. Scout scan chart 160 may display a history of scout scans, or a number of user-selected scout scans of interest. Once a user determines the proper location to begin primary MR acquisition (by using scout scans and/or reference images), current MR acquisition images are shown in image window 166.

Scan console screen 154 also includes common acquisition controls, such as buttons for setting scan prescriptions 168, adjusting the field of view (FOV) 170, adjusting slice thickness 172, setting a flip angle 174, controlling a timer 176, pausing acquisition 178, and other similar tools 180 and controls as known in the art. In addition, scan console screen 154 contains movement 182 and orientation 184 controls to adjust the current MR scan plane. Movement control 182 contains user inputs to set translation distances 186 and degrees of rotation 188. Therefore a user can acquire 2D projections at varying angles of the user's choice, for example. Alternatively, a number of preset orientations 184 for scan plane acquisition may include axial, sagittal, coronal, and other default positionings. Furthermore, an image may be defined as a reference plane or target plane 190 by which relative orientations of subsequent images may be determined.

Once a projection plane has been determined and other scan parameters set, a user can alter the contrast of the acquired image 192. As discussed above, it may be advantageous to set image contrast to display maximum light and dark contrast of an interventional device for later identification. Additionally, a user may request that an orthogonal projection be automatically acquired 196. Acquired projection images may then be saved for later examination 194 or stored as one of the 2D projections 198 to be used for a 3D reconstruction.

When 2D projections are set, a user may be shown a second GUI or reconstruction window 156. Reconstruction window 156 contains two image displays 200, 202 to show a user the 2D projections set for the 3D reconstruction. The 2D projections are loaded into the display windows using the load plane controls 204, 206. Though two displays 200, 202 are shown, it is appreciated that window 156 may adapt to display more than two images should additional 2D projections be selected 208. In this regard, reconstruction window 156 may alternatively contain thumbnails, scroll bars, and the like (not shown) for navigating amongst 2D projection images.

The identification of interventional devices in displayed 2D projection images as described above takes place when a user selects the device detection control 210. Device detection may be done automatically 212, in which case an algorithm of the interface 152 examines a selected 2D projection image 200 or 202 by row and/or column for areas of maximum contrast. Once the entire image has been examined, the areas displaying a maximum contrast value are deemed to be the interventional device. Alternatively, a user may manually 214 highlight, click on, or otherwise indicate the areas on 2D projection images 200, 202 which represent the interventional device. It is appreciated that combinations of the automatic 212 and manual 214 identification methods may be employed, such as user approval or adjustment of automatic detections. Also, in combination with identified points or lengths of an interventional device, the device's known geometry 216 may also be used in a 3D reconstruction. These geometries may be selected from a preset list by device type or loaded via a user input (not shown).

When a user selects the display device control 218, 3D reconstruction takes place. An image of the device's 3D shape and orientation may be displayed to a user in one or both of windows 200, 202, or in a separate window (not shown). With respect to the 3D image of the device, a user may select a scan plane of interest 220. As discussed above, this may involve selection from various orientations in a list, a drop-down menu, thumbnail representations, or the like (not shown). Once the plane of interest is selected 220, a user can have a scan plane rotational/translational matrix generated 222 and sent to the scanner 224 to cause the MR acquisition scan plane to be adjusted to the plane of interest with respect to the interventional device.

During the course of the interventional procedure, a user may wish to manually update the 3D image of the device 226. Alternatively, the user interface provides selections for automatic or continuous real-time updating 228 and for setting a periodic refresh rate of the 3D device image 230. Another option available during the procedure is to toggle between various amounts and types of surrounding or background anatomy displayed in the 3D device image 232.

For purposes of guidance, as described above, a target plane image may be loaded 234 from a previous acquisition. This target image may be displayed 236 in one or both of windows 200, 202, or may be displayed in a separate window (not shown). In a preferred embodiment, a user can select the guidance control 238 after the target image has been loaded and the 3D image of the plane of interest has been acquired. The guidance control 238 causes guidance visualizations such as shown and described with FIGS. 8, 9, 10, and 11 to appear. This may take the form of a new interface, or other known user interface conventions. The target plane image and scan plane image of the guidance visualization are updated based upon the user's selection of refresh style 226, 228, 230 for guidance during the procedure. In addition, it is appreciated that many variations and alternatives of user interface 152 may be useful and desired, and are contemplated by the present invention.

Therefore, the present invention embodies an MR system including gradient coils positioned about the bore of a magnet in order to generate a polarizing magnetic field, an RF transceiver system and switch controlled by a pulse module to transmit and receive signals to and from an RF coil assembly, and a computer to run a program which causes acquisition of 2D MR projections from the transceiver system and which then locates a continuous portion of an interventional device and an orientation of the device in three dimensions from the 2D projections.

In accordance with another embodiment of the invention, a method for tracking an interventional device includes the steps of acquiring two or more distinct MR images, locating an interventional device therein, determining a plane of interest with respect to the device, and adjusting image acquisition of the MR scanner to the plane of interest.

The present invention also encompasses an MR guidance interface stored on a computer readable storage medium. The interface includes an MR projection acquisition control, a device detection tool, a 3D reconstructor, a user input, and a guidance window. The device detection tool indicates the location of an interventional device in MR projections and the 3D reconstructor determines the 3D coordinates thereof. The user input allows a user to then define a scan plane with respect to the 3D coordinates. A display of the scan plane and a target plane is presented in a guidance window.

The present invention has been described in terms of the preferred embodiment, and it is recognized that equivalents, alternatives, and modifications, aside from those expressly stated, are possible and within the scope of the appending claims.

What is claimed is:

1. An MRI system comprising:
a plurality of gradient coils positioned about a bore of a magnet to impress a polarizing magnetic field;
an RF transceiver system and an RF switch controlled by a pulse module designed to transmit and receive RF signals to and from an RF coil assembly;
a computer having a program loaded thereon which, when executed by the computer, causes the computer to:
acquire a number of 2D MR projections from the transceiver system, the number of 2D MR projections being in acquisition planes at differing angles;
locate and determine an orientation of a continuous portion of an interventional device using the 2D MR projections;
define a scan plane of interest with respect to the location and orientation of the continuous portion of the interventional device;
determine a location and an orientation of a target plane of a scan subject; and
display a relationship of the scan plane of interest to the target plane.

2. The MRI system of claim 1 wherein the program further causes the computer to render a visualization of the continuous portion of the device, showing its location and orientation with respect to the target plane of the scan subject.

3. The MRI system of claim 1 wherein the program further causes the computer to automatically detect the device in the number of 2D MR projections and generate a set of 3D coordinates of the device therefrom.

4. The MRI system of claim 1 wherein the program further causes the computer to receive a manual device detection input configured to permit a user to manually identify the device in the number of 2D MR projections.

5. The MRI system of claim 1 further comprising a user input connected to allow a user to define the scan plane of interest.

6. The MRI system of claim 5 wherein the program further causes the computer to generate instructions causing MR data acquisition to re-orient into the scan plane of interest.

7. The MRI system of claim 6 wherein the program further causes the computer to periodically update the scan plane of interest to reflect movement of the continuous portion of the device.

8. The MRI system of claim 1 wherein the program causes the computer to acquire the number of 2D MR projections via the RF coil assembly positioned externally from an imaging object having the interventional device position therein.

9. The MRI system of claim 1 wherein the program causes the computer to acquire two substantially perpendicular 2D MR projections and to locate and determine the orientation of the continuous portion of the interventional device in 3D using only the two perpendicular 2 MR projections.

10. A method for tracking an interventional device comprising: acquiring at least two non-coplanar MR images; locating an interventional device in the at least two images; reconstructing a 3D shape and orientation of the interventional device from the at least two images; determining a plane of interest with respect to the device; and adjusting MR image acquisition to the plane of interest to track movement of the interventional device, wherein the target plane is defined by a desired eventual orientation for the device, favorable to an interventional procedure.

11. A non-transitory computer readable storage medium having an MR guidance interface stored thereon, the interface comprising:
   an MR projection acquisition control;
   a device detection tool configured to indicate a location of an interventional device in a first MR projection and a location of the device in a second MR projection;
   a 3D reconstructor programmed to determine 3D coordinates of the device from only the MR projections, without the use of RF coils embedded in the interventional device;
   a user input to define a scan plane with respect to the 3D coordinates of the device; and
   a guidance window configured to display the scan plane and a target plane.

12. The non-transitory computer readable storage medium of claim 11 wherein the first MR projection and the second MR projection are not coplanar.

13. The non-transitory computer readable storage medium of claim 12 wherein the interface further comprises a prompt to initiate acquisition of a third MR projection if the first and second MR projections are insufficient to determine one of a continuous shape or an orientation of the device.

14. The non-transitory computer readable storage medium of claim 12 wherein the interface further comprises a device geometry input.

15. The non-transitory computer readable storage medium of claim 11 wherein the interface further comprises at least one MR projection image display to visualize MR projection images acquired via the acquisition control.

16. The non-transitory computer readable storage medium of claim 15 wherein the device detection tool of the interface is further configured to receive manual identification of the device in the first MR projection and the second MR projection.

17. The non-transitory computer readable storage medium of claim 11 wherein the device detection tool of the interface further comprises an automatic detection tool using a contrast differentiation algorithm.

18. The non-transitory computer readable storage medium of claim 11 wherein the 3D reconstructor of the interface is further programmed to determine the 3D coordinates from only two MR projections.

19. The non-transitory computer readable storage medium of claim 11 wherein the 3D coordinates indicate a shape and an orientation of the device with respect to the target plane.

20. The non-transitory computer readable storage medium of claim 11 wherein the user input of the interface further comprises a selection tool indicating desired scan plane orientations relative to the device, including collinear with a major axis of the device, perpendicular to and intersecting a tip of the device, perpendicular to and ahead of a tip of the device, and encompassing the entire device.

* * * * *

UNITED STATES PATENT AND TRADEMARK OFFICE
CERTIFICATE OF CORRECTION

PATENT NO. : 9,002,433 B2
APPLICATION NO. : 11/532446
DATED : April 7, 2015
INVENTOR(S) : Aksit et al.

It is certified that error appears in the above-identified patent and that said Letters Patent is hereby corrected as shown below:

In the Claims

Col. 14, line 59 (Claim 9), delete "2 MR" and
substitute therefore -- 2D MR --.

Col. 14, line 65 (Claim 10), delete "device; and adjusting MR" and
substitute therefore -- device; adjusting MR --; and Col. 14, line 67 (Claim 10), delete "device," and
substitute therefore -- device; and visually guiding
repositioning of the interventional device towards a target
plane, --.

Signed and Sealed this
Twenty-second Day of September, 2015

Michelle K. Lee
*Director of the United States Patent and Trademark Office*